(12) United States Patent
Li et al.

(10) Patent No.: US 10,449,049 B2
(45) Date of Patent: Oct. 22, 2019

(54) PROSTHESIS FOR PREVENTING VALVE REGURGITATION

(71) Applicant: NINGBO JENSCARE BIOTECHNOLOGY CO., LTD., Ningbo, Zhejiang (CN)

(72) Inventors: Yibin Li, Zhejiang (CN); Shiwen Lv, Zhejiang (CN); Zhiyun Xu, Zhejiang (CN); Jianan Li, Zhejiang (CN); Deyuan Zheng, Zhejiang (CN); Zhi Chen, Zhejiang (CN)

(73) Assignee: NINGBO JENSCARE BIOTECHNOLOGY CO., LTD., Ningbo (CN)

( * ) Notice: Subject to any disclaimer, the term of this patent is extended or adjusted under 35 U.S.C. 154(b) by 78 days.

(21) Appl. No.: 15/401,818

(22) Filed: Jan. 9, 2017

(65) Prior Publication Data
US 2017/0112618 A1     Apr. 27, 2017

Related U.S. Application Data

(63) Continuation of application No. PCT/CN2015/080173, filed on May 29, 2015.

(30) Foreign Application Priority Data

Jul. 7, 2014   (CN) .......................... 2014 1 0322594

(51) Int. Cl.
*A61F 2/24* (2006.01)
*A61F 2/848* (2013.01)

(52) U.S. Cl.
CPC ............ *A61F 2/246* (2013.01); *A61F 2/2445* (2013.01); *A61F 2002/8483* (2013.01);
(Continued)

(58) Field of Classification Search
CPC ..... A61F 2/2442; A61F 2/2445; A61F 2/2454; A61F 2/246; A61F 2/2463
See application file for complete search history.

(56) References Cited

U.S. PATENT DOCUMENTS

2003/0204239 A1* 10/2003 Carlyle ................. A61L 29/085
623/1.11
2007/0239273 A1* 10/2007 Allen .................... A61F 2/2418
623/2.38
(Continued)

FOREIGN PATENT DOCUMENTS

CN     101902975 A     12/2010
CN     103079498 A     5/2013
(Continued)

OTHER PUBLICATIONS

International Search Report of PCT/CN2015/080173 dated Aug. 10, 2015.

*Primary Examiner* — Suba Ganesan
(74) *Attorney, Agent, or Firm* — Nixon Peabody LLP; Zhou Lu

(57) ABSTRACT

A prosthesis (100) for preventing a valve regurgitation, comprising a fixation unit (110), a connection piece (120) and a closure assisting piece (130); the fixation unit (110) comprises a fixation piece (111) and an anchor (112); the connection piece (120) is flexible, and a distal section thereof is connected to a proximal section of the fixation piece (111), and a proximal section thereof is connected to a distal section of the closure assisting piece (130); the fixation piece (111) is fixed on the atrial wall or a valve ring of a patient via the anchor (112); the deployed width of the fixation piece (111) is less than two-thirds of the circumference of a valve tissue annulus; the closure assisting piece (130) is located between autologous valve leaflets of the patient when in a free state; the maximum width of the
(Continued)

closure assisting piece (130) is less than the maximum deployed width of a single autologous valve leaflet; and the proximal end of the anchor (112) is provided with an anti-disengagement end (1120). The position of the prosthesis (100) can be adjusted, and the prosthesis (100) is accurately positioned and firmly anchored, and does not readily adhere to tissue adjacent to the valve annulus of the patient.

14 Claims, 15 Drawing Sheets

(52) U.S. Cl.
CPC ............ *A61F 2002/8486* (2013.01); *A61F 2210/0014* (2013.01); *A61F 2220/0016* (2013.01); *A61F 2220/0025* (2013.01); *A61F 2250/0004* (2013.01)

(56) References Cited

U.S. PATENT DOCUMENTS

| | | |
|---|---|---|
| 2009/0105751 A1 | 4/2009 | Zentgraf |
| 2011/0319989 A1 | 12/2011 | Lane et al. |
| 2012/0197388 A1 | 8/2012 | Khairkhahan et al. |
| 2013/0023985 A1 | 1/2013 | Khairkhahan et al. |
| 2013/0325110 A1 | 12/2013 | Khalil et al. |
| 2014/0067052 A1* | 3/2014 | Chau .................. A61F 2/246 623/2.11 |

FOREIGN PATENT DOCUMENTS

| | | |
|---|---|---|
| CN | 103338726 A | 10/2013 |
| CN | 104055600 A | 9/2014 |
| CN | 104055605 A | 9/2014 |
| WO | WO2006037073 A2 | 4/2006 |
| WO | WO2014039392 A1 | 3/2014 |

* cited by examiner

PROSTHESIS FOR PREVENTING VALVE REGURGITATION

CROSS-REFERENCE TO RELATED APPLICATION

The present application is a continuation application of PCT Patent Application No. PCT/CN2015/080173, entitled "PROSTHESIS FOR PREVENTING VALVE REGURGITATION", filed on May 29, 2015, which claims priority of Chinese patent application entitled "PROSTHESIS FOR PREVENTING VALVE REGURGITATION", filed on Jul. 7, 2014 having application number of 201410322594.8, the contents of which are hereby incorporated by reference.

TECHNICAL FIELD

The present invention belongs to medical device field, and in particular relates to a prosthesis for preventing valve regurgitation.

BACKGROUND

Mitral valve is located at the left atrioventricular orifice, and is consisted of five parts which are the valve annulus, the valve leaflets, the chordae tendineae, the papillary muscles, and the connecting junction, an exact name of which in anatomy is mitral apparatus or mitral complex.

Tricuspid valve is located at the right atrioventricular orifice, with three triangular like sail-shaped valves. The base of the valves is attached to the fibrous annulus at the atrioventricular orifice. By function, the fibrous annulus, the valves, the chordae tendineae, and the papillary muscles can be seen as a tricuspid valvar complex.

Mitral regurgitation can be divided into the following two kinds. 1. A rheumatic heart mitral regurgitation, mainly caused by mitral insufficiency, can cause a reverse flow of blood to mix different bloods, resulting in cardiac pumping and oxygen transfer function decrease. 2. A non-rheumatic mitral regurgitation usually referred to varying degrees of the mitral regurgitation caused by abnormalities, other than rheumatic valve diseases, of the mitral valve itself and its surrounding anatomical structures. The non-rheumatic mitral insufficiency has many causes, and the common causes are: leaflets prolapse, papillary muscle insufficiency or rupture of chordae, left atrial myxoma, valve annulus calcification, congenital valve malformation, infective endocarditis, and so on. The mitral regurgitation can also be divided into three types, functional, degenerative, or mixed. The most common one is the degenerative and the functional mitral regurgitations. The functional mitral regurgitation is generally secondary to a left ventricular wall motion dysfunction, a left ventricular dilatation, and a papillary muscle dysfunction, generally found in patients with heart failure. This part of patients also has, secondary to a coronary heart disease, ischemic mitral regurgitation and non-ischemic heart muscle disease related mitral regurgitation. The degenerative mitral regurgitation disease is generally deemed to be pathological changes in the valve structure, or pathological changes of the structure below the valve, including an abnormal extension or rupture of the chordae.

Tricuspid regurgitation is usually caused by a pulmonary hypertension, a right ventricular dilatation, and a tricuspid annulus expansion. After the tricuspid regurgitation occurs, the symptoms of a right heart failure such as fatigue, ascites, edema liver pain, indigestion, anorexia, and so on become worse. Tricuspid insufficiency is mainly divided into functional tricuspid insufficiency and organic tricuspid insufficiency. The organic insufficiency of the valves caused by rheumatic fever is rare. The major cause is the functional insufficiency, and the most common cause is the right ventricular dilatation and the tricuspid annulus expansion caused by the pulmonary hypertension, resulting in tricuspid valve relative insufficiency, however the valves themselves are normal in structure, such as the rheumatic mitral valve disease, the congenital cardiovascular disease, and the pulmonary heart disease.

Traditional treatment for the mitral regurgitations and tricuspid regurgitations includes drug therapy for the mild to severe regurgitations, and surgical approach corresponding to surgical indications. Among them, the surgical approach also includes mitral valve replacements and tricuspid valve replacements, and mitral valve repairs and tricuspid valve repairs. For the simple mitral regurgitation, only 30% of the patients have the need of the mitral valve replacement, the rest only need the mitral valve repair. In the surgical approach, the typical thoracotomy and open heart surgery are too invasive, which need to establish a cardiopulmonary bypass, with higher incidence of complications and risk of infection. To reduce the risk of surgery, transcatheter interventional replacement and repair methods are developed.

According to the report of an article, [Enriquez-Sarano M, Schaff H V, Orszulak T A, et al. Valve repair improves the outcome of surgery formitral regurgitation: a multivariate analysis [J]. Circulation, 1995, 91 (4): 1022-1088], the visible replacement surgery has a higher overall mortality rate and a lower survival rate.

TABLE 1

Comparison of mortality rate and complications after a mitral valvuloplasty and a mitral valve replacement (multicenter)

|  | Mitral valvuloplasty | Mitral valve replacement | P |
| --- | --- | --- | --- |
| Overall surgical death rate | 2.6% | 10.3% | 0.0002 |
| Death rate for age <75 years | 1.3% | 5.7% | 0.036 |
| Death rate for age >75 years | 6.8% | 30.8% | 0.0005 |
| 5-year survival rate | 92% | 72% | 0.003 |
| 10-year survival rate | 69% | 58% | 0.0004 |
| Thrombosis incidence | 1.8% | 8% | 0.03 |
| Postoperative cardiac function (left ventricular ejection fraction) | 54% | 49% | 0.05 |
| 10-year no surgery rate | 75% | 80% | 0.47 |
| Endocarditis within 4.5 years | 0 | 2.8% | 0.08 |

The current problems to be solved for the transcatheter treatment of the valve regurgitation are as follows: the implantation volume is to be reduced under the premise of as far as possible to ensure the anti-regurgitation effect; the anti-regurgitation device must be accurately positioned and firmly fixed at the location needed to be treated; the anti-regurgitation device is required to minimize an effect on normal function of the rest valve leaflets; the anti-regurgitation device needs to adapt to the differences in the physiological structures of the valve annulus. The following lists technical points of different anti-regurgitation devices in prior art.

WO 2006037073 A2 describes a therapy method of mitral valve repair using a mitral clip to suture a center or a corner region of the mitral valve, but this technique cannot be applied to the following two types of patients: one of which has a systole coapting gap between valve leaflets>10 mm, as cannot accurately synchronize the movements of the two valve leaflets; and the other of which has a severe thickening and calcification of the structure below the annulus, due to the breaking risk of the chordae for the pressure increase of the chordae, the valve leaflets, and the valve annulus.

US2009105751A1 and CN101902975 describe an apparatus for repairing a valve leaflet in a pulsatile heart of a patient, comprising a handle assembly, a capture assembly, and a needle. A valve leaflet is captured through the capture assembly, and the needle passes through the valve leaflet to limit the movement of the prolapse valve leaflet to achieve the anti-regurgitation effect. But in operation, this technique needs to seize the moving valve leaflet, the operation is difficult and time consuming, and easy to cause laceration on the autologous valve leaflet.

US20130023985 describes an implant, an implant system, and a method for treating valve mal-coaptation and other valve diseases. The implant includes a coaptation assist body, and the length of the superior edge of the coaptation assist body contacting the autologous annulus is 25-35 mm, which is equal to the distance between the first commissure and the second commissure. The length of the coaptation assist body between the superior edge and the inferior edge is 50-60 mm. On the coaptation assist body, an anchoring device can be optionally provided. In one claim, it defines that a part of the coaptation assist body is cone shaped, and in another claim, besides defining the length of the superior edge of the coaptation assist body contacting the autologous annulus is 25-35 mm, it further defines that a height of the leaflet coaptation perpendicular to the valve annulus is 35-45 mm, a height of the non-coaptation of the ventricle in the direction perpendicular to the annulus is 25-35 mm, and an curve radius of the coaptation is within 35-45 mm. The limiting for the length of the superior edge contacting the autologous annulus of the system is only for the overall repair of the anterior leaflet prolapse or posterior leaflet prolapse of the mitral valve, and the repair of an overall valve leaflet prolapse of a part of the tricuspid valve. It also shows that the inferior edge of the coaptation assist body covers at least a majority of the leaflets, and the coaptation has a specific curve requirement. This technique cannot accommodate the repair of the prolapse of a small part of the valve, or the repair of smaller valves such as the aortic valve. While repairing the mal-coaptation position, it sacrifices the rest normal valves. In summary, the disadvantages include: first, it clearly describes that the length of the superior edge of the coaptation assist body equals the distance between the first commissure and the second commissure, and thus it is applicable only to the overall repair of the valve leaflets, the repair area including not only the leaflet prolapse part but also the normal part of the leaflet; second, the length of the annulus varies widely among persons, and before the actual operation, the distance between the first commissure and the second commissure is unpredictable, the product design is hard to have an exact match; third, the shape of a part of the coaptation assist body is cone shaped, striving to match the cone shape of human leaflets, and for the same reason among different persons, the exact match is difficult to achieve; fourth, the design is not suitable for the repair of the commissural leaflets prolapse.

In CN103338726A, a method for treating mal-coaptation of a the patient's heart valve is described, which comprises introducing an implant into the heart while the implant is in a first configuration, deploying the implant from the first configuration to a second configuration within the heart, the implant in the second configuration having a coaptation assist body with first and second opposed coaptation surfaces; and supporting the deployed implant so that the coaptation assist body is offset from the axis of the heart valve along the coaptation zone. In one claim, the method also includes: selectively deploying a first anchor at a first target location near the first commissure (the first commissure is at a first junction of the first and second leaflets of the heart valve); selectively deploying a second anchor at a second target location near the second commissure (the second commissure is at a second junction of the first and second leaflets of the heart valve); and introducing a coaptation assist body into the heart. In another claim, it describes the implant comprises a coaptation assist body, a first anchor, and a second anchor, the coaptation assist body has an axis and first and second opposed major coaptation surfaces, each coaptation surface extending laterally between a first lateral edge and a second lateral edge of the coaptation assist body; the first anchor selectively deployable at a first target location of the heart near the first commissure and coupleable to the coaptation assist body so that the first lateral edge is oriented toward the first commissure; the target location of the second anchor is near the second commissure. In another claim, it further limits that the axis of the implant extends along the axis of the valve, and the first and second lateral sides of the coaptation assist body extend along the curve of the coaptation zone of the heart valve, wherein the coaptation assist body of the supported implant is sufficiently laterally conformable so that engagement between the implant and the heart laterally bends the coaptation assist body between the edges toward the curve defined by the coaptation zone of the heart valve. The above described claims limit that the target positions of the anchors are near the first and second commissures, and the overall coaptation assist body is sufficiently laterally conformable to the heart valve. This technique does not adapt for a partial valve prolapse syndrome, and has the following disadvantages while exhibiting the anti-regurgitation effect. First, the "supporting the deployed implant so that the coaptation assist body is offset from the axis of the heart valve along the coaptation zone" means that as the implant naturally deploys, the coaptation assist body shrinks along a centerline, which requires the coaptation assist body to be cone shaped. Second, the coaptation assist body covers the non-prolapse normal valve, and in the long-term movement, is likely to cause an adhesion, sacrificing the normal operation of the normal part of the valve. Third, during the opening and closing processes, the autologous valve near the autologous annulus and toward the apex of the heart has a smaller motion amplitude than a valve leaflet located close to the cusp, and is easily adhered to the heart valve assist body which is sufficiently laterally conformable and contact to the autologous valve. This location is different from the superior edge of the coaptation assist body, which is at the location of the valve annulus. The location of the valve annulus should grow together with the autologous annulus during the long-term implantation to improve the fixation effect. However, once adhesion occurs to the autologous valve near the autologous annulus and toward the apex of the heart, the valve leaflet movement is affected, easily causing a second regurgitation, which leads failure of the anti-regurgitation treatment. Fourth, the valve annulus has different size for different person, leading the requirement for producing numerous specifications of products.

US20130325110A1 describes a beating heart method of delivering a valve leaflet coaptation assist prosthesis to treat the mitral and tricuspid regurgitations. The method comprises using a flexible rail to delivering a ventricular anchor from atrium through autologous valve to the right ventricle to perform the anchoring; using a catheter to deliver the prosthesis and adjust the location of the prosthesis at the tricuspid annulus till the regurgitation decreases; fixing the position of the catheter relative to the flexible rail and securing the catheter to the subclavian vein. This method of delivery can adjust the position of the prosthesis to adapt to different regurgitation position, and has a disease adaptability, but the location of the fixation position at the subclavian vein is far away from the valve annulus position, easily leads unstable of the fixation and a prosthesis displacement after the fixation.

The current clinical results show that there is no ideal product for the treatment of the valve regurgitation. The main reason is that the mitral annulus, the tricuspid annulus, etc. have special physiological structures, and there is a complex physiological environment at the position below the annulus, resulting in difficulty of accurate positioning and fixing of the products. In addition, the valve prolapse has different degree and location. For example, some of the patients have the mitral insufficiency caused by an anterior leaflet prolapse, and some of the patients have the mitral insufficiency caused by a commissural leaflets disease. During the treatment of the insufficiency at the pathologic change location, the above-mentioned techniques also interfere with the physiological structure of the rest normal mitral valve, lacking of disease adaptability. In summary, although the techniques described above have respective effects on the valve repair, there is a need for the prosthesis in the field of surgical treatment of valvular insufficiency, and the prosthesis is position adjustable, positioning accurate, and anchoring secure, that is able to deal with a variety of different degrees and locations of the lesion.

SUMMARY OF THE INVENTION

An object of the present invention is to overcome limitations of prior art and to provide a prosthesis for preventing valve regurgitation for a partial valve prolapse. The position of the prosthesis of the present invention can be adjusted, and the prosthesis is accurately positioned and firmly anchored, and does not readily adhere to tissue adjacent to the valve annulus of the patient, and is capable of adjusting a location of the prosthesis based on different degrees and locations of disease, then performing a positioning and an anchoring.

The object of the present invention is achieved by following technical solution:

A prosthesis for preventing valve regurgitation comprises a fixation unit, a connection piece and a closure assisting piece, the fixation unit comprising a fixation piece and an anchor, a distal section of the connection piece is connected to a proximal section of the fixation piece, a proximal section of the connection piece is connected to a distal section of the closure assisting piece, the connection piece is flexible such that the connection piece and the closure assisting piece connected thereto are movable with a movement of a valve leaflet, the fixation piece is secured to an atrial wall or a valve annulus of a patient by the anchor, a deployed width of the fixation piece is less than two thirds of a circumference of the valve tissue annulus, the closure assisting piece is between autologous valve leaflets of the patient when in a free state, a maximum width of the closure assisting piece is less than a maximum deployed width of a single autologous valve leaflet, a proximal end of the anchor is provided with an anti-disengagement end.

The object of the present invention can also be further achieved by following technical solutions:

In some embodiments, a sum of a length of the closure assisting piece and a length of the connection piece is greater than a deployed height of the autologous valve leaflet.

In some embodiments, the closure assisting piece is a single piece, multiple pieces, a sleeve, a bag, a column, or a balloon, or the closure assisting piece is a combination of the single piece and the multiple pieces, or the closure assisting piece is a combination of the single piece and the sleeve, or the closure assisting piece is a combination of the single piece and the bag, or the closure assisting piece is a combination of the single piece and the column, or the closure assisting piece is a combination of the single piece and the balloon.

In some embodiments, the closure assisting piece is a grid structure, or the closure assisting piece is a polymer piece or an animal-derived material piece, the closure assisting piece is provided with a hole when the closure assisting piece is the polymer piece or the animal-derived material piece.

In some embodiments, the anchor is connected to the fixation piece.

In some embodiments, the fixation piece and the connection piece are integrated as one piece.

In some embodiments, a length of the closure assisting piece along an axis of a plane of the valve annulus is larger than or equal to 10 mm, and smaller than or equal to 60 mm.

In some embodiments, a length of the connection piece along an axis of a plane of the valve annulus is larger than or equal to 1 mm, and smaller than or equal to 25 mm.

In some embodiments, there is a channel for blood flowing therethrough between the closure assisting piece and the fixation piece.

In some embodiments, the connection piece is in a form of sheet, strip, or filament, or the connection piece is a combination of the above-mentioned structures.

In some embodiments, the connection piece is partially covered with a film, and a portion of the connection piece which is not covered with the film is the channel for blood flowing therethrough.

In some embodiments, the connection piece is entirely covered with a film, a hole/holes is/are provided in the film, and the hole is the channel for blood flowing therethrough.

In some embodiments, when the connection piece is a single strip or a single filament, both sides of the connection piece are the channel for blood flowing therethrough.

In some embodiments, the fixation piece is a flexible polymer sheet or a polymer mesh.

In some embodiments, the fixation piece has a frame structure consisting of a plurality of support rods; or the frame structure is a waved structure or a zigzag structure made of metallic shape memory material wire; or the frame structure is formed in a lattice pattern; or the frame structure is a combination of the above-described structures.

In some embodiments, crests and troughs of the waved structure or tips of the zigzag structure are wound into circles.

In some embodiments, the frame structure is made of shape memory material formed by weaving or integrated cutting.

In some embodiments, adjacent rods of the frame structure are twisted with each other to form a compact structure.

In some embodiments, in the free state, the distal section of the frame structure is an arc shaped structure along a circumference of the valve annulus.

In some embodiments, the frame structure is covered with a film, the film is connected to the frame structure through sintering, welding, gluing, or stitching, a material of the film comprises PTFE, polyethylene, polypropylene, polyester, or an animal-derived material.

In some embodiments, the distal section of the closure assisting piece is stitched to the proximal section of the connection piece by a suture, or a plurality of rod wires extend out from the distal end of the closure assisting piece, the plurality of rod wires are twisted to the proximal section of the connection piece, or the distal end of the closure assisting piece is connected by sintering to the proximal section of the connection piece.

In some embodiments, the distal section of the connection piece is stitched to the proximal section of the fixation piece by a suture, or a plurality of rod wires extend out from the distal end of the connection piece, and the plurality of rod wires are twisted to the proximal section of the fixation piece, or the distal end of the connection piece is connected by sintering to the proximal section of the fixation piece.

In some embodiments, the closure assisting piece is provided with an adjusting member, the adjusting member is a metal wire or a polymer wire, one end of the metal wire or the polymer wire is connected to the closure assisting piece, and the other end of the metal wire or the polymer wire is connected to a ventricle or an apex of a heart.

In some embodiments, the proximal end of the closure assisting piece is provided with a deploying device, and the deploying device is a wire made of metal or polymer, to prevent the closure assisting piece from wrinkling or to prevent the closure assisting piece from being compressed to reduce size. In some embodiments, the deploying device is a rod member, or the deploying device is a waved structure or a zigzag structure made of metallic shape memory material wire.

In some embodiments, a most distal end of the anchor is a sharp, and a distal section of the anchor is in a preset shape, the distal section of the anchor is pre-shaped into one or a combination of following shapes: a spiral, a circle, an arc, a combination of an arc line and a straight line, a bifurcated double hook, a 3D curved form, a multi-segment curved form, the distal end of the anchor has no barbs, has a barb, or has a plurality of barbs.

Comparing with prior art, the present invention has advantages:

1. Different from the overall valve replacement technology, the present invention retains the autologous valve leaflets and the leaflet movement function, prevents reversing of the prolapse valve leaflets by the closure assisting piece, so as to achieve the purpose of preventing valve regurgitation, which has advantages of less implant volume, better blood dynamics, and so on.

2. The maximum width of the closure assisting piece of the present invention is smaller than the maximum deployed width of the single autologous leaflet, which can not only avoid the influence on the closing function of other adjacent valve leaflets caused by an over-wide closure assisting piece, but also make circumferential adjustment in order to place the closure assisting piece in the most suitable prolapse position, which not only has less implant volume, but also has lower complications, and it adapts to annulus sizes for different patients, the indication can be expanded, and the manufacturer can reduce the product specification.

3. The maximum width of the closure assisting piece according to the present invention is smaller than the maximum deployed width of the single autologous leaflet, the autologous leaflet includes both the anterior and posterior leaflets, and the commissural leaflets, the application scope is wider than that of the prior art.

4. The connection piece of the present invention is flexible so that the connection piece and the closure assisting piece connected therewith can move with the movement of the valve leaflets without affecting the movement function of the autologous valve leaflets.

5. In the present invention, a blood flowing channel is supplied between the closure assisting piece and the fixation piece, which can prevent adhesion between the prosthesis and a tissue near the patient's valve annulus due to a long-term contact.

6. In the present invention, the fixation piece adopts a non-closed structure (the width of the fixation piece is less than two thirds of the circumference of the valve tissue annulus), thereby reducing the support force to the atrial wall and avoiding affection to the atrium and the movement function of the adjacent valves.

7. The product of the present invention has a simple design and structure, and a low manufacturing cost.

8. The present invention retains the function of the autologous valve leaflets, so that the operation risk is low, and the durability of the valve leaflets is good.

9. In some embodiments of the invention, an adjusting member is also provided. In Image-Aided, the effect of the valve leaflet anti-regurgitation can be controlled and adjusted until the best effect, and then the adjusting member is fixed to the apex of the heart and the ventricular wall.

DETAILED DESCRIPTION

In order to make the objectives, technical schemes and advantages of the present disclosure more apparent and better understood, the present disclosure will be described in more details with reference to the accompanying figures and embodiments.

The distal end as described in the present disclosure refers to the end farther from the apex of the heart, and the proximal end refers to the end nearer to the apex of the heart.

EXAMPLE 1

Figure 1A:
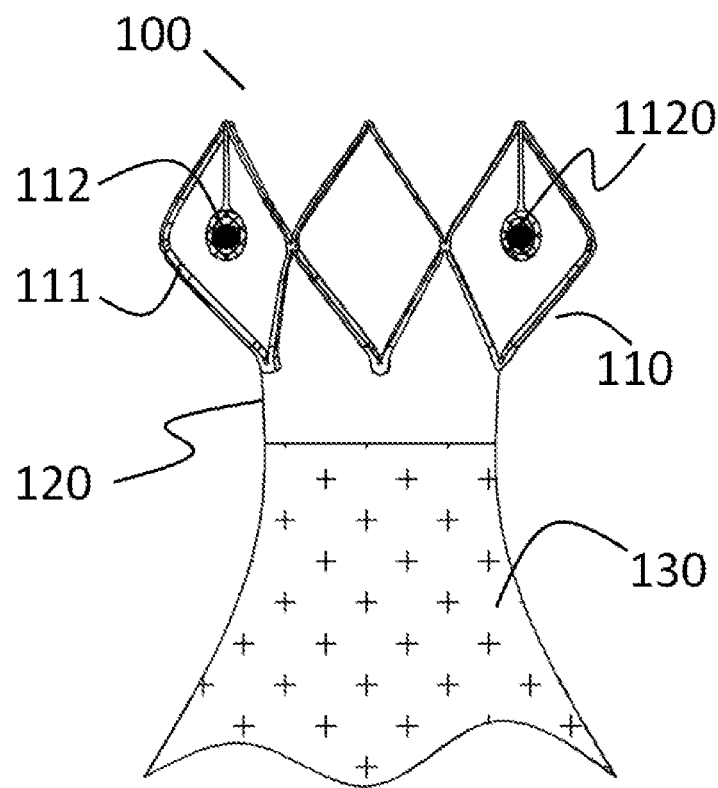
FIG. 1A and FIG. 1B show schematic views of one embodiment of the present invention.
Figure 1B:
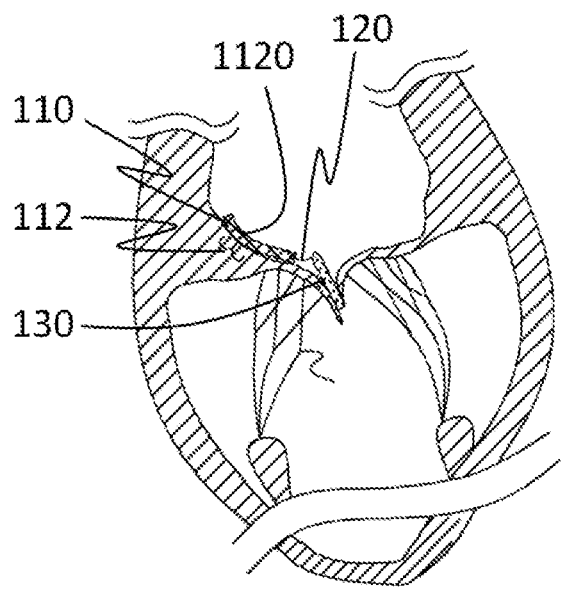

Referring to FIG. 1A and FIG. 1B, a prosthesis 100 for preventing valve regurgitation comprises a fixation unit 110, a connection piece 120, and a closure assisting piece 130.

The fixation unit 110 comprises a fixation piece 111 and at least two anchors 112. A distal section of the connection piece 120 is connected to a proximal section of the fixation piece 110. A proximal section of the connection piece 120 is connected to a distal section of the closure assisting piece 130. The connection piece 120 is flexible so that the connection piece 120 and the closure assisting piece 130 connected thereto can move along with the movement of the valve leaflets. There is a channel for blood flowing therethrough between the closure assisting piece 130 and the fixation piece 111. The fixation piece 111 is a polymer sheet, or the fixation piece 111 has a frame structure. The fixation piece 111 is fixed to an atrial wall or a valve annulus of a patient by the anchors 112. A width of the deployed fixation piece 111 is less than two thirds of a circumference of the valve tissue annulus. The closure assisting piece 130 is between autologous valve leaflets of the patient when in a free state. A maximum width of the closure assisting piece 130 is less than a maximum width of a single deployed autologous valve leaflet. A most distal end of the anchor 112 is a sharp. A distal section of the anchor 112 is in a preset shape. A proximal end of the anchor 112 is provided with an anti-disengagement end 1120. In one embodiment, the prosthesis 100 for preventing the valve regurgitation is used to treat the mitral valve prolapse. A length of the closure assisting piece 130 along an axis of a plane of the valve annulus is about 50 mm, the advantage of which is to ensure that at least a portion of the closure assisting piece 130 is located between the anterior leaflet and the posterior leaflet. Two surfaces of the closure assisting piece 130 attach respectively to the anterior leaflet and the posterior leaflet, so as to have the mitral valve prolapse caused by the chordae rupture be treated, thereby effectively preventing the mitral regurgitation.

Figure 2A:
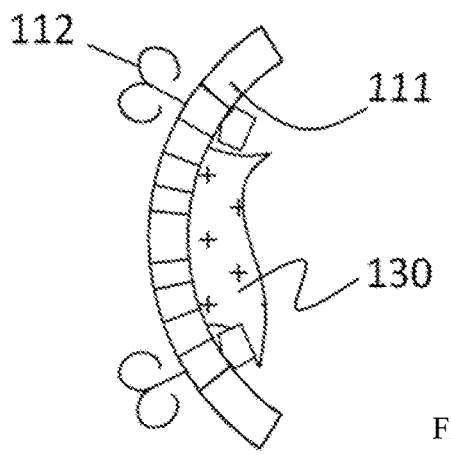
FIG. 2A and FIG. 2B show schematic views of another embodiment of the present invention.
Figure 2B:
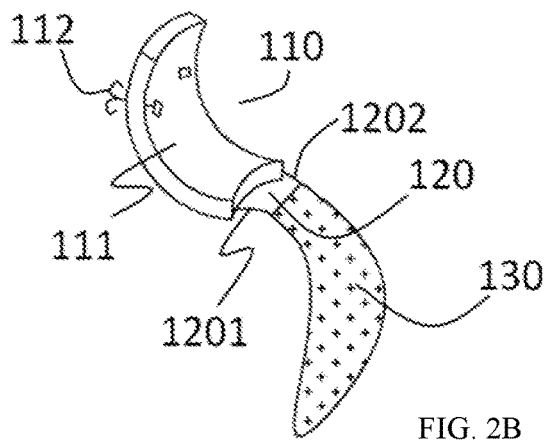
Figure 2C:
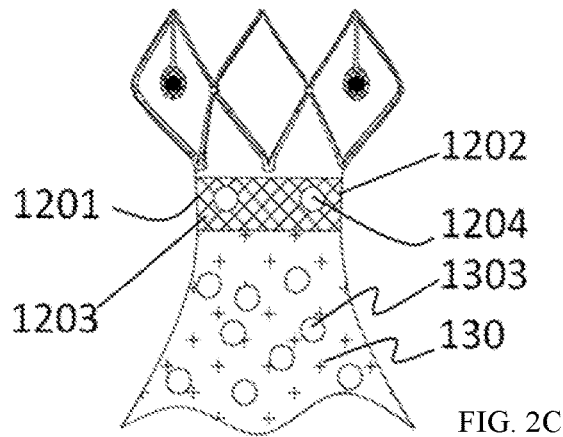
FIG. 2C and FIG. 2D show schematic views of two embodiments of the closure assisting piece respectively.
Figure 2D:
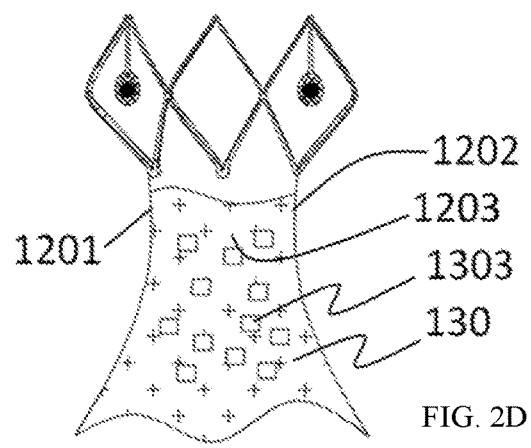

Referring to FIG. 2A and FIG. 2B, in the free state, the fixation piece 111 is a flexible polymer sheet, and the distal section of the fixation piece 111 is an arc structure along the circumferential direction of the valve annulus. The advantage of this design is that the fixation piece 111 is allowed to better attach to the patient's atrial wall or valve annulus, assisting physician to determine the location at the beginning of the deployment, and the anchor 112 is not easy to displace when it is anchored. In one embodiment, a length of the connection piece along an axis of the plane of the valve annulus is 15 mm. The connection piece 120 is flexible, and the connection piece 120 is composed of two rods 1201 and 1202. The rods 1201 and 1202 have a linear shape. For the reason that during the opening and closing of the valve leaflets, a motion range of the valve leaflets near the valve annulus is very small, an adhesion may be caused due to a long-term contact of the connection piece 120 with the autologous valve leaflets. In the present invention, a gap formed between the rods 1201 and 1202 allows the blood to flow therethrough. On the one hand, an opening area for blood supplying increases, and on the other hand, the adhesion between the connection piece 120 and the autologous valve leaflets can be prevented. In one embodiment, the distal end of the closure assisting piece 130 is joined to the proximal section of the connection piece 120 by sintering, and the distal end of the connection piece 120 is joined to the proximal section of the fixation piece 111 by sintering. When the fixation piece 111 is anchored to the patient's atrial wall or valve annulus, the connection piece 120 is flexible, so that the connection piece 120 and the closure assisting piece 130 connected thereto can move with a movement of the valve leaflet, while closure assisting piece 130 is still able to have sufficient space for adjustment in the axial direction of the valve annulus, so that the closure assisting piece 130 can be better attached to the autologous valve leaflets when the valve leaflets close, to improve the effect of preventing valve regurgitation. In another embodiment, the closure assisting piece 130 is a grid structure (not shown) woven from metal wires (in some embodiments, the metal wires are nickel-titanium memory alloy wires). In another embodiment, as shown in FIG. 2C, the closure assisting piece 130 is a polymer material sheet or an animal-derived material sheet. When the closure assisting piece 130 is the polymer material sheet or the animal-derived material sheet, the closure assisting piece 130 is provided with holes 1303, and each hole 1303 has a circular shape. The maximum width of the closure assisting piece 130 is smaller than the maximum width of a single deployed valve leaflet. The autologous valve leaflets comprise anterior, posterior, and commissural leaflets. The prosthesis of the present invention has a broader application scope than prior art. A sum of the length of the closure assisting piece 130 and the length of the connection piece 120 is greater than the height of the deployed valve leaflet. In some embodiments, between the rod 1201 and the rod 1202 of the connection piece 120 is partially covered with a film 1203, and the film is connected to the rods 1201, 1202 by welding, gluing, or stitching, and the portion that is not covered with the film is the channel for blood flowing therethrough. In some embodiments, the area between the rods 1201, 1202 is covered with the film 1203, and the film 1203 is provided with holes 1204, and each hole 1204 is a passage through which the blood flows. This design is to further prevent the adhesion of the connection piece 120 to the autologous valve leaflet. As shown in FIG. 2D, the closure assisting piece 130 is provided with holes 1303, and each hole 1303 has a polygonal shape. In one embodiment, the area between the rods 1201, 1202 are completely covered with the film 1203, the film 1203 and the closure assisting piece 130 are made of the same material, and are connected to each other by stitching, welding, or the like.

Figure 3A:
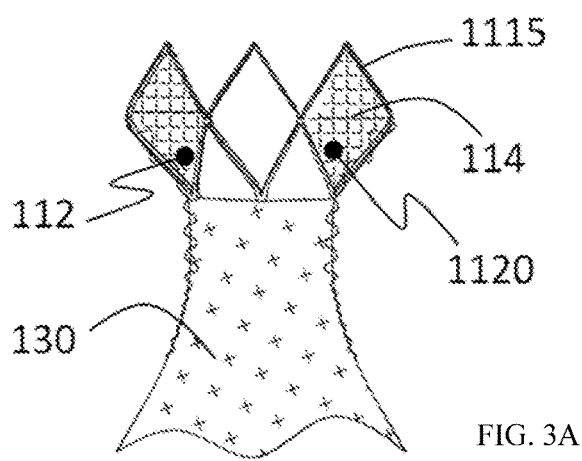
FIG. 3A to FIG. 3D show schematic views of a plurality of embodiments of the present invention respectively.
Figure 3B:
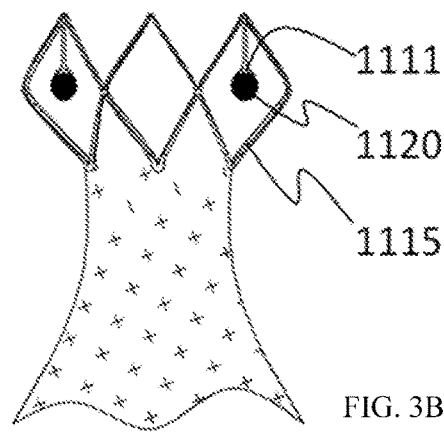
Figure 3C:
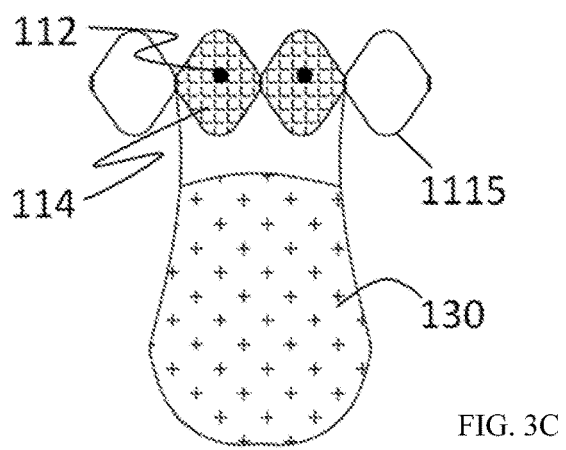
Figure 3D:
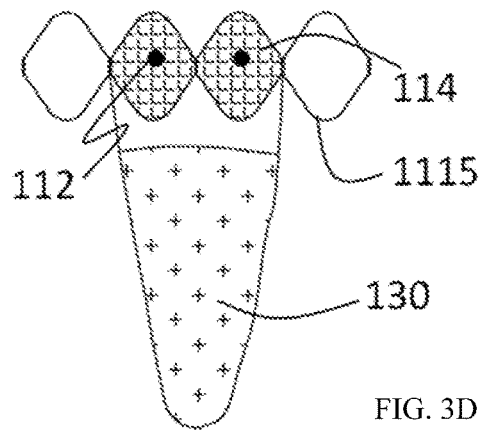

Referring to FIG. 3A to FIG. 3D, the fixation piece 111 has a frame structure 1115. In the free state, a distal section of the frame structure 1115 an arc structure along a circumferential direction of the valve annulus, the advantage is that the fixation piece 111 is attached better to the patient's atrial wall or valve annulus. The frame structure 1115 is covered with a film 114 that is joined to the frame structure 1115 by sintering, welding, gluing, or stitching. The material of the film 114 includes PTFE, polyethylene, polypropylene, polyester, or animal derived materials. In one embodiment, as shown in FIG. 3A, the frame structure 1115 is formed in a lattice pattern, and the frame structure 1115 is formed by integrally cutting from a metallic memory alloy material. The frame structure 1115 is partially covered with the film. The anchor 112 penetrates the film 114 to secure the frame structure 1115 on the atrial wall or the valve annulus of the patient. The frame structure 1115 is located between the anti-disengagement end 1120 of the anchor 112 and patient's tissue. In another embodiment, as shown in FIG. 3B, the frame structure 1115 is formed in a lattice pattern, and the frame structure 1115 is integrally cut from a shape memory material. The frame structure 1115 is provided with a hole 1111. The proximal end of the anchor 112 is provided with the anti-disengagement end 1120 having a diameter larger than the diameter of the hole 1111. The anchor 112 goes through the hole 1111 to secure the frame structure 1115 on the atrial wall or the valve annulus of the patient. In yet another embodiment, as shown in FIG. 3C and FIG. 3D, the frame structure 1115 is woven from a shape-memory material. The present invention can select a corresponding width of the closure assisting piece 130 according to the width of the prolapse valve leaflets, to diminish the implant volume without affecting the movements of the rest valve leaflets with normal function, thereby decreasing the companion. As shown in FIG. 3C, the width of the proximal section of the closure assisting piece 130 is greater than the width of the distal section of the closure assisting piece 130, and is suitable for a larger leaflet prolapse region. As shown in FIG. 3D, the width of the proximal section of the closure assisting piece 130 is smaller than the width of the distal section of the closure assisting piece 130, and is suitable for a smaller leaflet prolapse region, such as the commissural leaflet region.

EXAMPLE 2

Figure 4A:
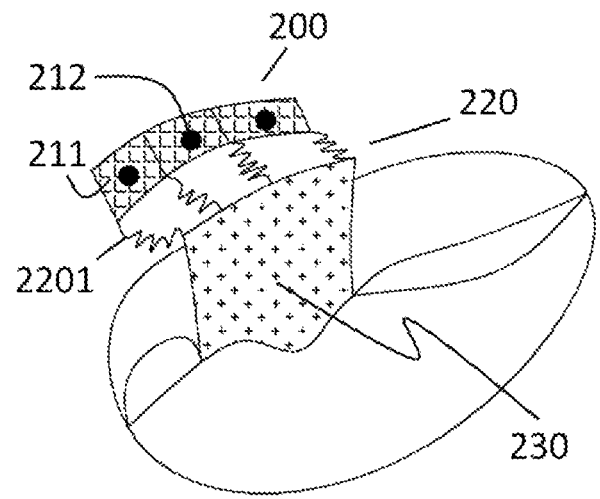
FIG. 4A and FIG. 4B show schematic views of yet another embodiment of the present invention.
Figure 4B:
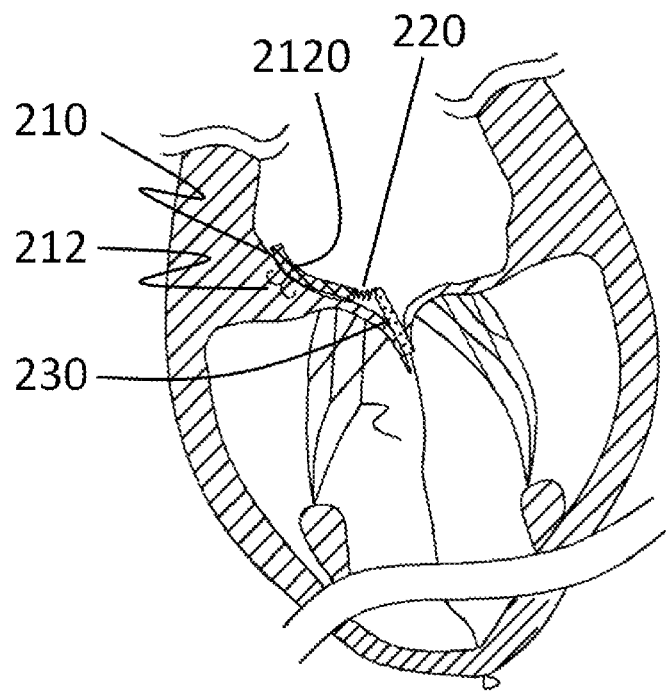

Referring to FIG. 4A and FIG. 4B, a prosthesis 200 for preventing valve regurgitation comprises a fixation unit 210, a connection piece 220, and a closure assisting piece 230. The fixation unit 210 comprises a fixation piece 211 and at least two anchors 212. A distal section of the connection piece 220 is connected to a proximal section of the fixation member 210. A proximal section of the connection piece 220 is connected to a distal section of the closure assisting piece 230. The connection piece 220 is flexible so that the connection piece 220 and the closure assisting piece 230 connected thereto can move along with the movement of the valve leaflets. There is a channel for blood flowing therethrough between the closure assisting piece 230 and the fixation piece 211. The fixation piece 211 is a polymer mesh or the fixation piece 211 has a frame structure. The fixation piece 211 is fixed to the patient's atrial wall or the valve annulus by the anchor 212. The deployed width of the fixation piece 211 is less than two thirds of the circumference of the valve tissue annulus. The closure assisting piece 230 in the free state is between the patient autologous valve leaflets. The maximum width of closure assisting piece 230 is less than the maximum width of a single deployed autologous valve leaflet. A most distal end of the anchor 212 is a sharp, a distal section of the anchor 212 is in a preset shape, a proximal end of the anchor 212 is provided with an anti-disengagement end 2120. In one embodiment, the prosthesis 200 for preventing valve regurgitation is used to treat mitral valve prolapse. The connection piece 220 is composed of four rods 2201, the rods 2201 are curve shaped, and such design can enhance the compliance of the connection piece 220 so that the connection piece 220 and the closure assisting piece 230 connected thereto can move with the movement of the valve leaflet, preventing the adhesion of the connection piece 220 and the closure assisting piece 230 to the valve annulus or the autologous valve leaflets during the long-term contact therewith.

Figure 5A:
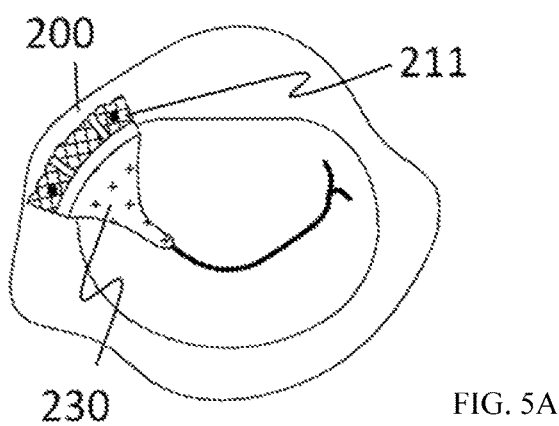
FIG. 5A to FIG. 5D show schematic views of positioning adjustment of the deployed fixation piece along a circumferential direction of a patient's valve annulus.
Figure 5B:
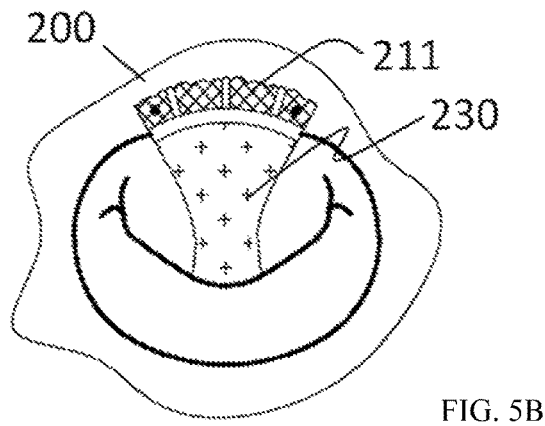
Figure 5C:
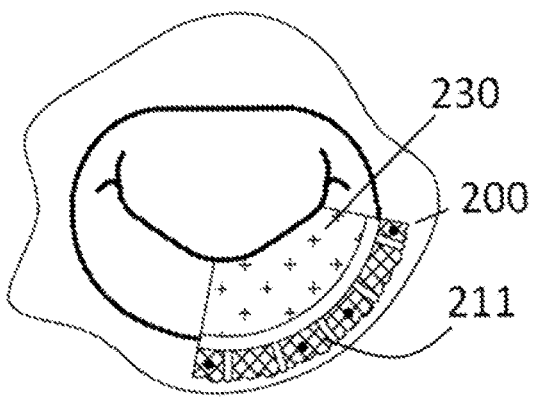
Figure 5D:
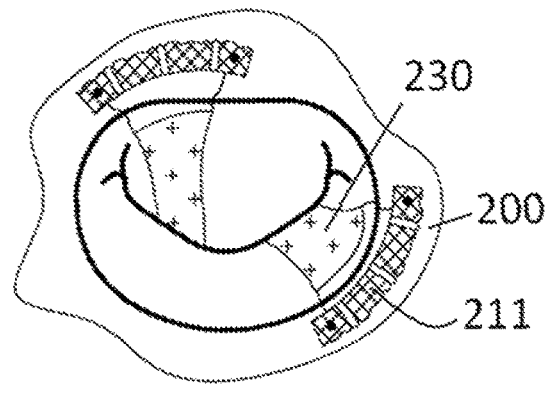

Referring to FIG. 5A to FIG. 5D, different from the complete ring-structured products in prior art, after the fixation piece 211 is deployed, the position of the fixation piece 211 can be adjusted along the circumferential direction of the valve annulus of the patient, such as the position of the commissural leaflet (FIG. 5A), the position of the anterior leaflet(FIG. 5B), or the position of the posterior leaflet (FIG. 5C), until the operator determines the position as the most appropriate anti-regurgitation position. Then based on the attaching situation between the closure assisting piece 230 and the autologous leaflet, the fixation piece 211 is anchored in the position by releasing the anchor 212 to achieve a fixation between the prosthesis 200 and autologous tissue. It truly achieves an accurate treatment of the disease, while retaining normal physiological function of the rest heart valves, and reducing the interference of the normal functioning heart valves. The present invention also achieves that the position of the prosthesis can be adjusted, and the prosthesis is accurately positioned, firmly anchored, and disease adapted, and can prevent newly occurred paravalvular leakage because of the pressure applied on the commissural leaflet. When the patient has the leaflet prolapses in many different locations, for the conventional complete ring shaped products, due to the confined space, the use of the closure assisting piece with a larger area will suppress the normal autologous valve leaflets to be closed, and the use of a smaller area closure assisting piece will not achieve a desirable treatment effect. In the present invention, the deployed fixation piece 211 has a smaller width, which allows the surgeon to implant multiple devices to different lesion locations, as shown in FIG. 5D, to enhance the effect of preventing valve regurgitation.

Figure 6A:
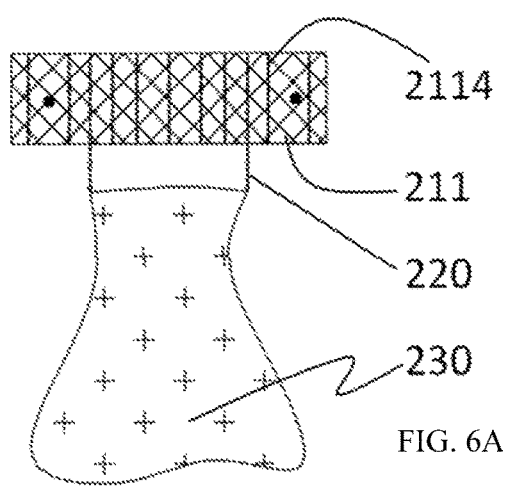
FIG. 6A to FIG. 6P respectively show schematic views of a plurality of embodiments of the present invention.
Figure 6B:
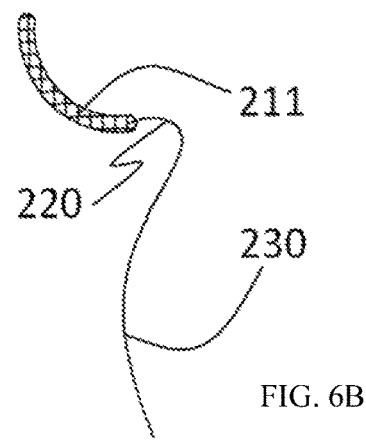
Figure 6C:
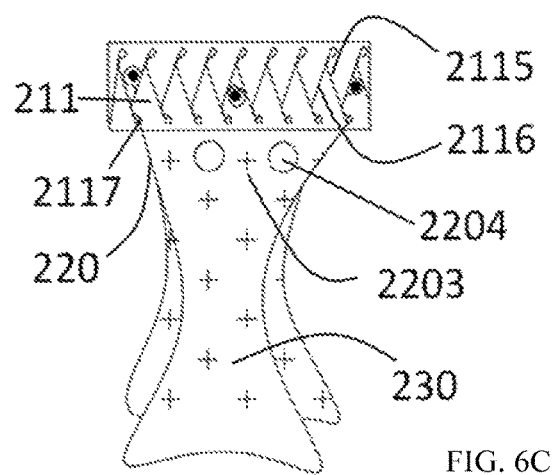
Figure 6D:
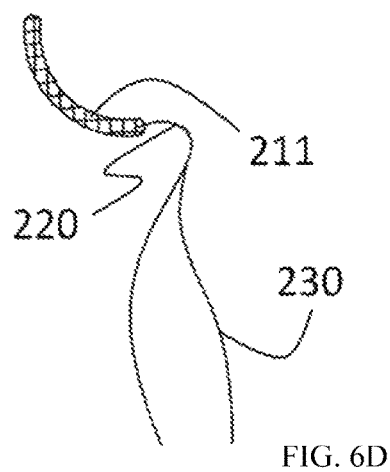
Figure 6E:
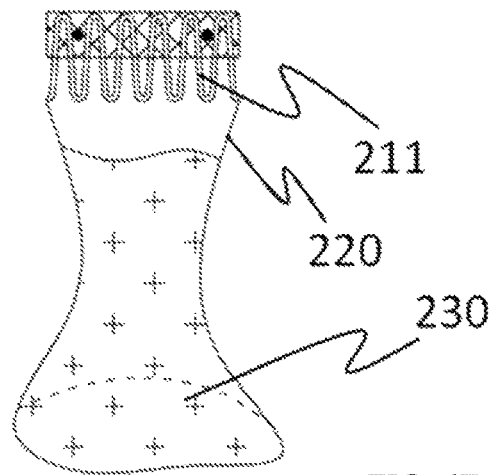
Figure 6F:
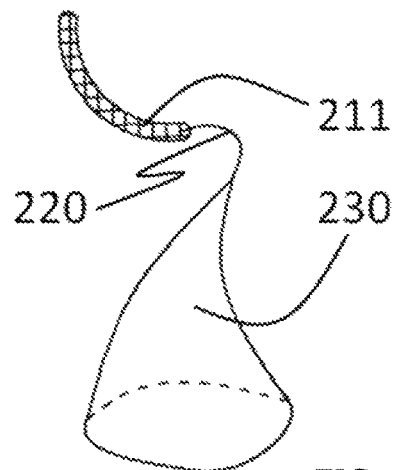
Figure 6G:
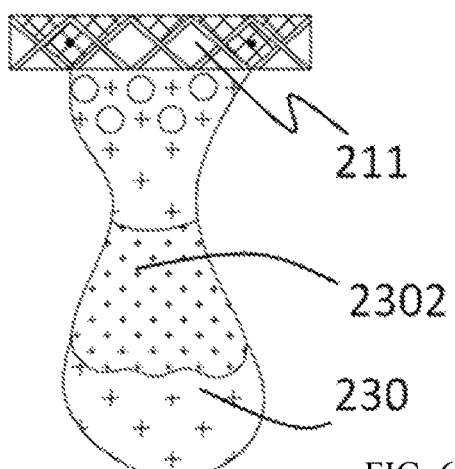
Figure 6H:
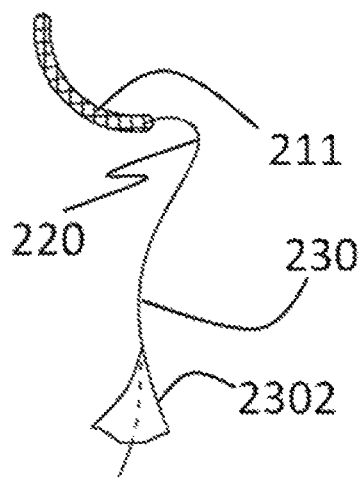
Figure 6I:
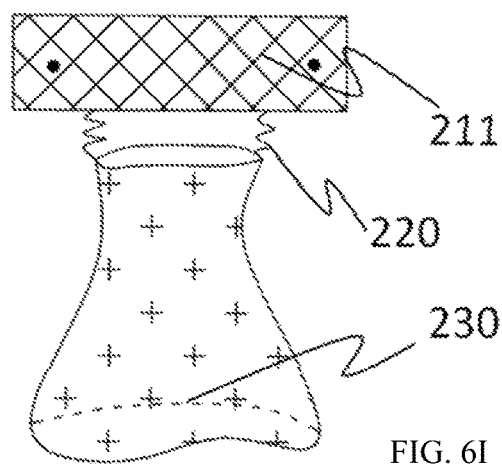
Figure 6J:
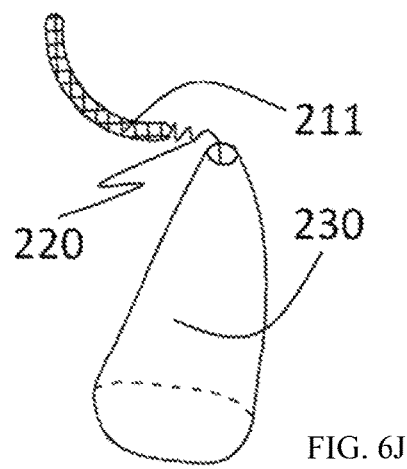
Figure 6K:
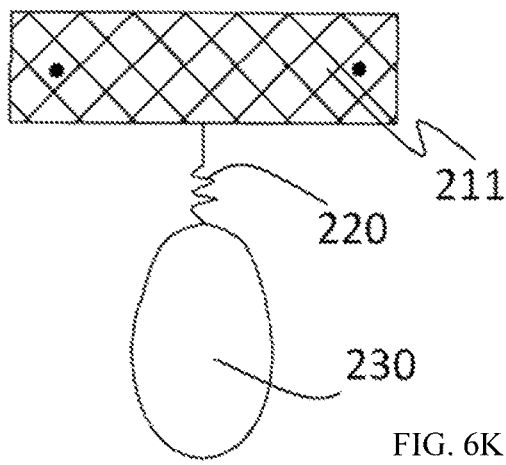
Figure 6L:
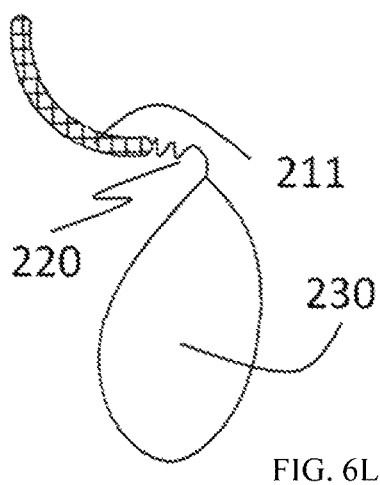
Figure 6M:
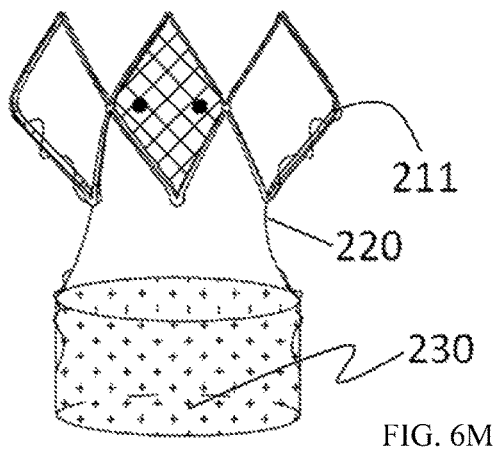
Figure 6N:
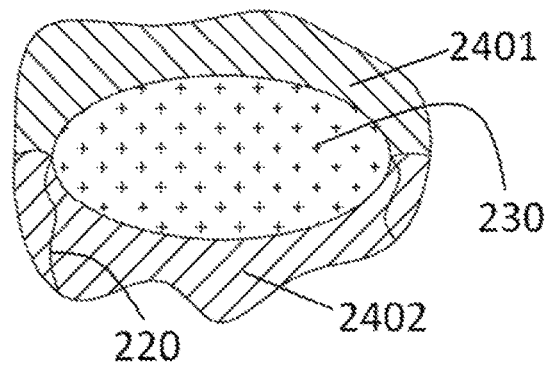
Figure 6O:
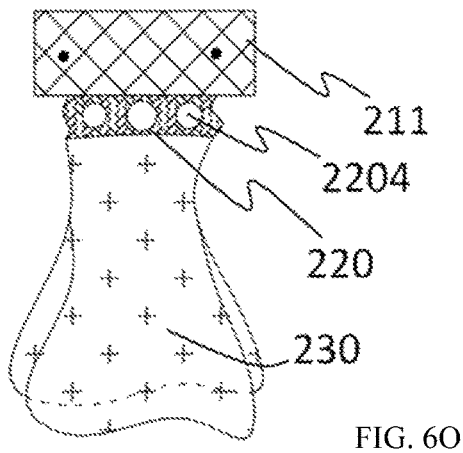
Figure 6P:
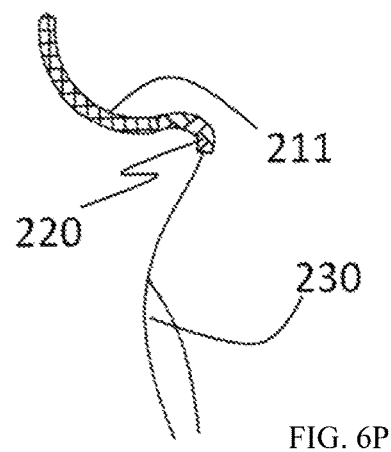

Referring to FIG. 6A and FIG. 6B, in another embodiment, the fixation piece 211 has a frame structure, and the frame structure are entirely covered by a film. The frame structure is comprised of a plurality of support rods 2114. The support rods 2114 are arranged in an arc shape along the circumferential direction of the valve annulus. The proximal ends of two of the support rods 2114 extend to form the connection piece 220. The closure assisting piece 230 is a single piece. The distal end of the closure assisting piece 230 is connected to the proximal section of the connection piece 220 by sintering. Referring to FIG. 6C to FIG. 6H, in various embodiments, the frame structure is a waved structure or a zigzag structure formed by winding a metallic memory material wire. As shown in FIG. 6C and FIG. 6D, the adjacent rods 2115, 2116 of the frame structure are twisted with each other to form a compact structure. The advantage of the design is to enhance the deployed strength of the fixation piece 211, and to maintain the deployed shape to not easy to wrinkle due to the blood wash and the tissue movement. The connection piece 220 is comprised of two rods, and the connection piece 220 is entirely covered with the film 2203. The film 2203 is provided with a hole 2204, and the hole 2204 is a channel through which the blood flows. The distal section of the connection piece 220 is stitched to the proximal section of the fixation piece 211 by suture. In some embodiments, the crests and troughs of the waved structure or tips of the zigzag structure are wound into circles 2117. The advantage of this design is that the strength is greater in the seam of the stitching, and the securing between the connection piece 220 and the fixation piece 211 is firmer. The closure assisting piece 230 has two pieces, which is advantageous in making it more completely attached with the autologous valve leaflets, and in better anti-regurgitation. The closure assisting piece 230 is made of the same material as the film 2203, and the closure assisting piece 230 and the film 2203 are joined to each other by sintering. As shown in FIG. 6E and FIG. 6F, the closure assisting piece 230 has a bag shape. One end (the distal end) of the bag is connected together, and the other end (proximal end) of the bag opens. When the blood flows from the ventricle to the atrium, the bag shaped closure assisting piece is bulged to increase a contact area to the autologous valve leaflet. When the blood flows from the atrium to the ventricle, the bag shaped closure assisting piece is deflated, which does not affect the blood flow. As shown in FIG. 6G and FIG. 6H, a bag member 2302 is provided on the closure assisting piece 230. The distal end and both sides of the bag member 2302 are sealed, and the proximal end opens. When the blood flows from the ventricle to the atrium, the bag member 2302 is bulged to increase a contact area to the autologous valve leaflet. When the blood flows from the atrium to the ventricle, the bag member 2302 is deflated, which does not affect the blood flow. In other embodiments, as shown in FIGS. 6I and 6J, the closure assisting piece 230 has a sleeve shape, and the connection piece 220 is comprised of two rods which are curved in shape, so as to increase the flexibility of the connection piece 220. The fixation piece 211 is a polymer sheet which is designed to improve the flexibility of the fixation piece 211, and to facilitate the attachment to the atrial wall. A passage through which the blood flows is formed between the two rods. Referring to FIG. 6K and FIG. 6L, the connection piece 220 is consisted of a single filament, and a shape of the filament is a combination of a straight line and a curved line, so that the flexibility of the respective portions of the connection piece 220 can be different. Both sides of the connection piece 220 are blood flowing channels. The closure assisting piece 230 is a balloon. The surgeon can place the balloon into the patient's lesion. The balloon can be inflated by a flushing solution, and the amount of the flushing is adjusted so that the degree of inflation of the balloon can be adapted to the actual regurgitation of the valve leaflet of the patient. Referring to FIG. 6M and FIG. 6N, a plurality of rod wires extended from the distal end of the connection piece 220, are wound around and connected to a proximal section of the fixation piece 211. A plurality of rod wires extended from the distal end of the closure assisting piece 230, are wound around and connected to the proximal section of the connection piece 220. In some embodiments, the rod wires extend from the closure assisting piece 230 to the fixation piece 211. In some embodiments, the closure assisting piece 230 has a column shape, and the cross-section of the closure assisting piece 230 is oval, so that the closure assisting piece 230 can be maximally attached to the autogenous valve leaflets 2401, 2402 of the patient. In order to reduce the weight of the closure assisting piece 230, the closure assisting piece 230 is filled with a lightweight material such as expanded PTFE or the like. The outer surface of the closure assisting piece 230 is coated with a relatively dense polymer material to prevent the tissue growth covering the closure assisting piece 230 and adhering the closure assisting piece 230 with the valve leaflet. Referring to FIG. 6O and FIG. 6P, the connection piece 220 is a polymer sheet, and the connection piece 220 is provided with holes 2204, and the holes 2204 are blood flowing passages. This design is advantageous to improve the flexibility of the connection piece 220 to prevent adhesion. The closure assisting piece 230 is a combination of a single piece and a pair of pieces. The proximal end of the single piece is fixedly connected to the distal end of the pair of pieces, which is also for better attaching of the closure assisting piece 230 with the autologous valve leaflet to increase the attaching area and improve the preventing regurgitation effect.

Figure 7A:
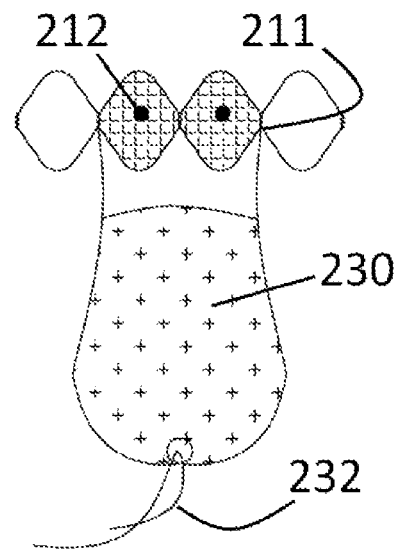
FIG. 7A and FIG. 7C show schematic views of a plurality of embodiments of the closure assisting piece respectively.
Figure 7B:
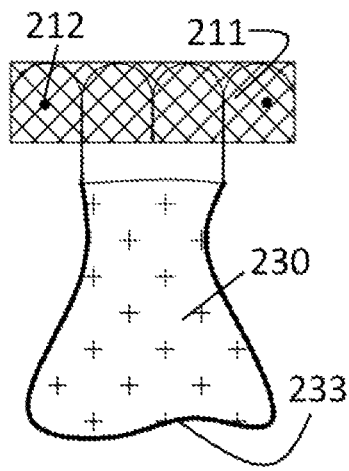
Figure 7C:
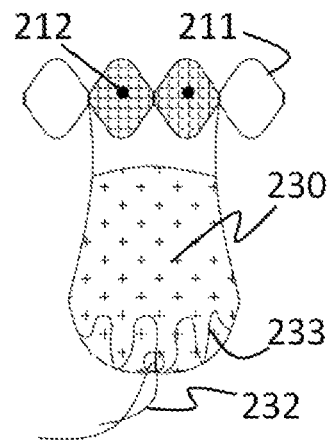

Referring to FIG. 7A, in one embodiment, the closure assisting piece 230 is provided with an adjusting device 232. The adjusting device 232 is a metal wire. One end of the metal wire is connected to the closure assisting piece 230, and the other end of the metal wire is connected to the ventricle or the apex of the heart. The advantage of this design is that, in Image-Aided, the surgeon can control and adjust the anti-regurgitation effect of the valve leaflet by adjusting the metal wire during surgery. The other end of the metal wire is fixed to the ventricular wall or the apex of the heart when the minimal regurgitation of the valve is achieved (i.e., the anti-regurgitation effect is the best), and the closure assisting piece 230 can be prevented from reversing into the atrium during the moving of the valve leaflet. In another embodiment, referring to FIG. 7B, the proximal end of the closure assisting piece 230 is provided with a deploying device 233 made of a metal wire or a polymer wire to prevent the closure assisting piece 230 wrinkled. The deploying device 233 extends from the distal end of the closure assisting piece 230 to the proximal end of the closure assisting piece 230. The rigidity of the deploying device 233 makes the closure assisting piece 230 less prone to wrinkling under the impact of a blood flow. In another embodiment, referring to FIG. 7C, the deploying device 233 is a rod, or a waved structure or a zigzag structure formed by winding a metallic memory material wire to prevent wrinkling of the closure assisting piece 230. In another embodiment, the deploying device is provided at the proximal end of the sleeve shaped or bag shaped closure assisting piece 230 to prevent the closure assisting piece 230 from being compressed resulting in downsizing.

EXAMPLE 3

Figure 8A:
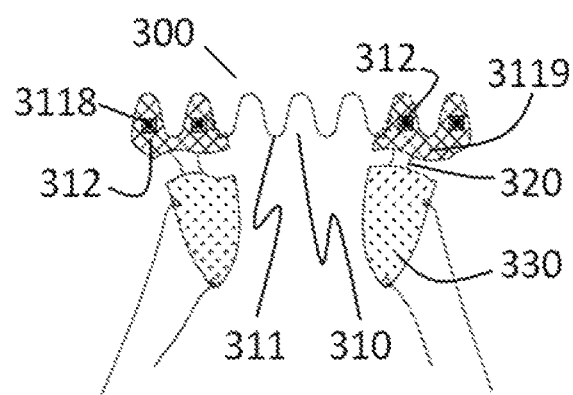
FIG. 8A shows a schematic view of yet another embodiment of the present invention.
Figure 8B:
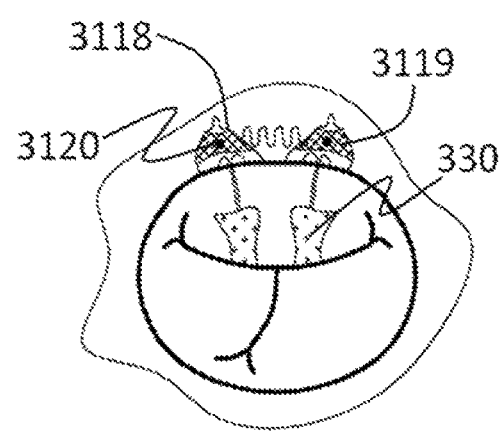
FIG. 8B to FIG. 8D show schematic views of a plurality of embodiments of the present invention used in the tricuspid repair respectively.
Figure 8C:
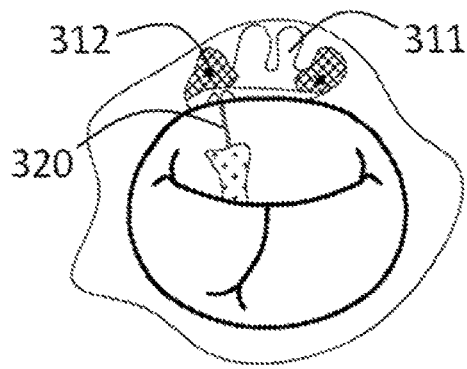
Figure 8D:
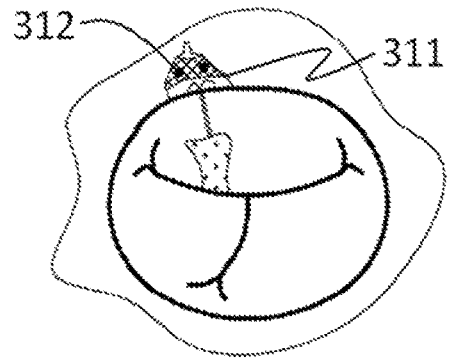

Referring to FIG. 8A and FIG. 8B, a prosthesis 300 for preventing valve regurgitation comprises a fixation unit 310, a connection piece 320, and a closure assisting piece 330. The fixation unit 310 comprises a fixation piece 311 and at least two anchors 312. A distal section of the connection piece 320 is connected to a proximal section of the fixation unit 310. A proximal section of the connection piece 320 is connected to a distal section of the closure assisting piece 330. The connection piece 320 is flexible so that the connection piece 320 and the closure assisting piece 330 connected thereto can move with the movement of the valve leaflets. There is a blood flowing channel between the closure assisting piece 330 and the fixation piece 311. The fixation piece 311 is a polymer sheet, or the fixation piece 311 has a frame structure. The fixation piece 311 is fixed to the atrial wall or the valve annulus of the patient by the anchor 312. The deployed width of the fixation piece 311 is smaller than two thirds of a circumference of the valve tissue annulus. A part or all of the closure assisting piece 330 in the free state is between the patient's autologous valve leaflets. The maximum width of the closure assisting piece 330 is smaller than a maximum deployed width of a single autologous valve leaflet. The distal end of the anchor 312 is a sharp. The distal section of the anchor 312 is in a preset shape. The proximal end of the anchor 312 is provided with an anti-disengagement end 3120. In one embodiment, the prosthesis 300 for preventing valve regurgitation is used to treat tricuspid valve prolapse. Referring to FIG. 8A, the frame structure consists of a plurality of support rods and a waved structure formed by winding metallic memory material wires. The support rods on both sides of the frame structure are covered with films to form two film covering regions 3118, 3119. The two film covering regions 3118, 3119 are connected by waved metallic memory material. Two anchors 312 are located on each film covering regions 3118, 3119. This design is particularly suitable for the patient who has a situation of multiple valve leaflet prolapses occurring in different locations. It only needs to adjust the distance between the anchors 312 to dispose the closure assisting piece 330 at different target locations, which saves time for re-implanting the device, and is also different from the conventional large area anti-regurgitation piece, preventing repressing the normal autologous valve leaflets to close, and enhancing the valve anti-regurgitation effect. Referring to FIG. 8C and FIG. 8D, the operator decides the most appropriate anti-regurgitation position, and then anchors to release the anchor 312 to achieve a fixation between the fixation piece 311 and the autologous tissue. It truly achieves, while accurate treating the lesions, retaining the normal physiological function of the rest heart valves, and reducing the interference to the normal operation of the heart valve. It also achieves that the position of the prosthesis can be adjusted, and the prosthesis is accurately positioned, firmly anchored, and disease adapted; and it is adaptive to valve annulus sizes of different patients, and has a wide application scope.

Figure 9A:
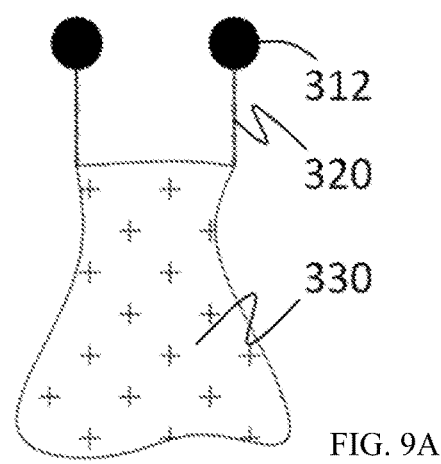
FIG. 9A to FIG. 9H show schematic views of a plurality of embodiments of the present invention respectively.
Figure 9B:
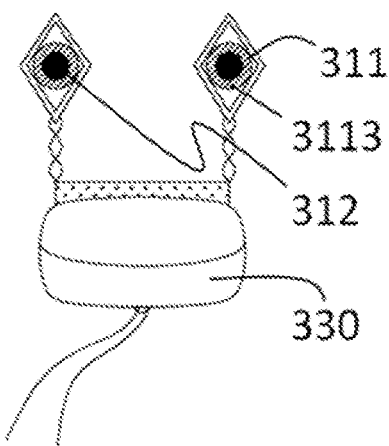
Figure 9C:
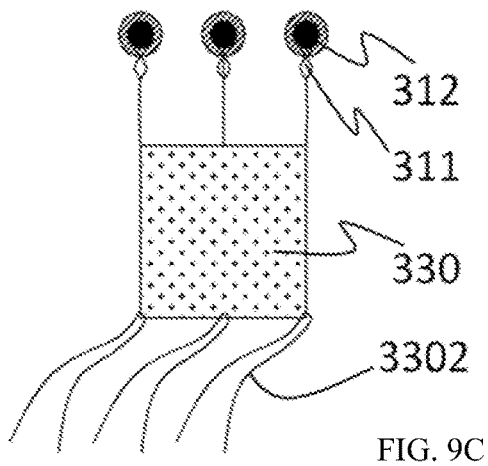
Figure 9D:
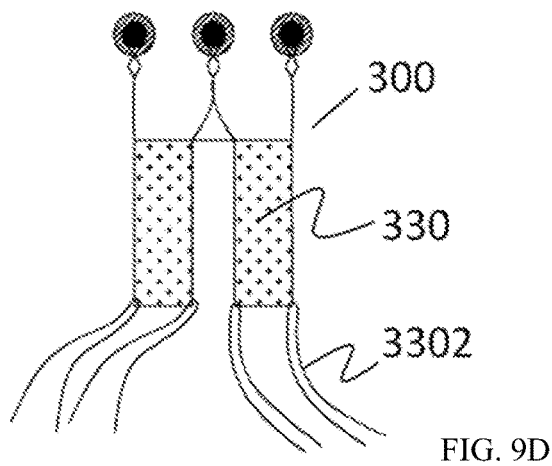
Figure 9E:
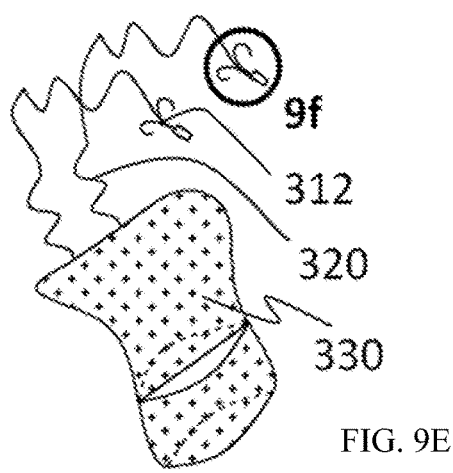
Figure 9F:
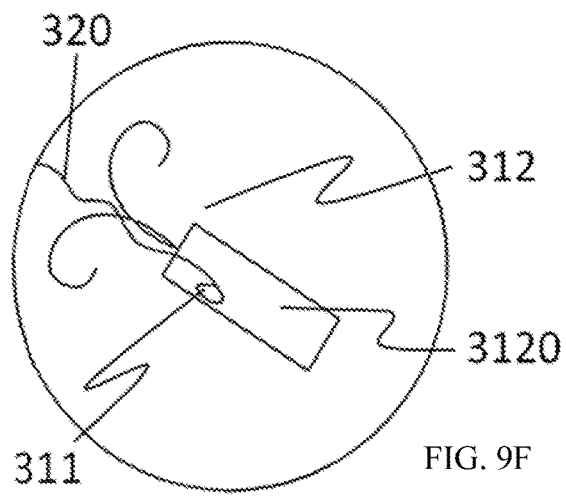
Figure 9G:
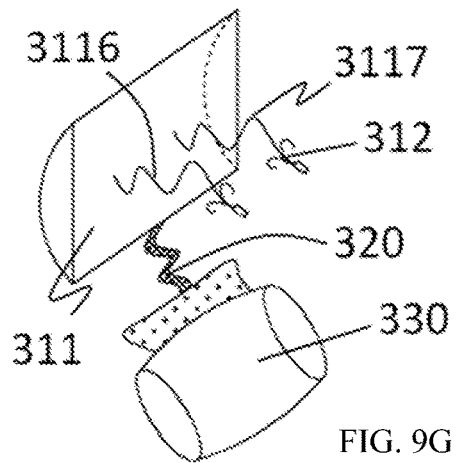
Figure 9H:
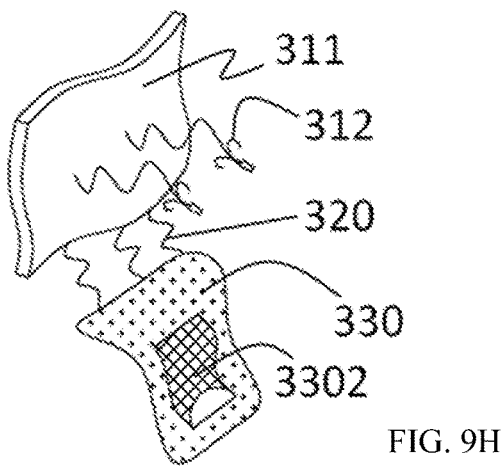

In various embodiments, as shown in FIG. 9A to FIG. 9H, the anchor 312 is connected to the fixation piece 311. The advantage of this design is that there is no need to consider the alignment problem between the anchor 312 and the fixation piece 311 when it needs to release the anchor 312 to fix the fixation piece 311 to the autologous tissue, and the design can ensure the accurate alignment and anchoring, simplify the surgical process, and save the operation time. Referring to FIG. 9A, the fixation piece has an annular frame structure (not shown in the drawing), the anchor 312 is fixedly connected to the annular frame structure, the distal section of the connection piece 320 is connected to the annular frame structure, and the proximal section of the connection piece 320 is connected to the distal section of the closure assisting piece 330. Referring to FIG. 9B, the fixation piece 311 has a frame structure, and the frame structure is a grid stent. The frame structure is covered with a film 3113, and the anchor 312 is connected to the film 3113. The closure assisting piece 330 is a combination of a single sheet and a balloon. The balloon has a surface made of a sparse porous material, and contains a water-swellable material therein, which is expanded in the blood to attach to the patient valve leaflet. Referring to FIG. 9C, the fixation piece 311 is a polymer sheet, and the anchor 312 is connected to the polymer sheet. A plurality of polymer wires 3302 are connected to the closure assisting piece 330. One end of the polymer wires 3302 is connected to the closure assisting piece 330 and the other end is connected to the ventricle or the apex of the heart. The doctor adjusts the polymer wires 3302 so that the closure assisting piece 330 does not affect the normal closing of the valve leaflets and prevents the regurgitation. Referring to FIG. 9D, the prosthesis 300 for preventing valve regurgitation comprises two closure assisting pieces 330 respectively provided with polymer wires 3302, for adjustment and preventing the reversing. Referring to FIG. 9E and FIG. 9F, the connection piece 320 is composed of two wires, and the distal end of the connection piece 320 is connected to the fixation piece 311. The fixation piece 311 is a ring wound from a metal wire. The fixation piece 311 and the distal end of the connection piece 320 are integrally formed and both located in the anti-disengagement end 3120 of the anchor 312. The closure assisting piece 330 is a combination of a single piece and a sleeve. Referring to FIG. 9G, the anchor 312 is connected to the fixation piece 311 through two wires 3116, 3117. The fixation piece 311 is a polymer sheet. The connection piece 320 is a strip. Both sides of the connection piece 320 are the blood flowing channels. The closure assisting piece 330 is a combination of a single piece and a column. Referring to FIG. 9H, the closure assisting piece 330 is a combination of a single piece and a bag. The bag 3302 is sealed at its distal end and both sides, and has an opening at its proximal end. When the blood flows from the ventricle to the atrium, the bag 3302 is bulged to increase a contact area to the autologous valve leaflet. When the blood flows from the atrium to the ventricle, the bag 3302 is deflated, which does not affect the blood flow. The fixation piece 311 is a polymer sheet, and the fixation piece 311 is connected to the closure assisting piece 330 through the connection piece 320. The connection piece 320 is composed of three curved rods.

Figure 10A:
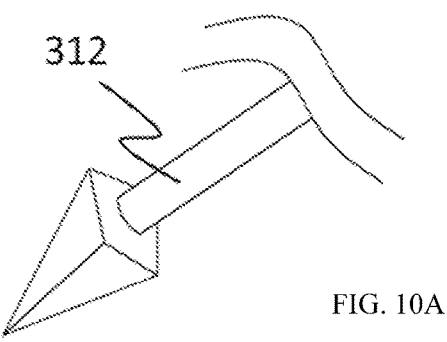
FIG. 10A to FIG. 10F show schematic views of a plurality of embodiments of the anchor respectively.
Figure 10B:
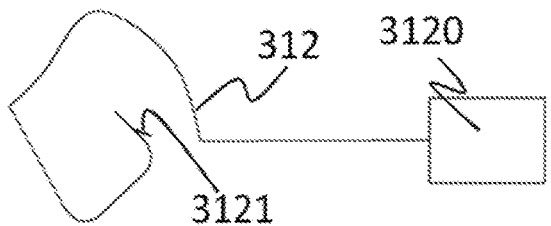
Figure 10C:
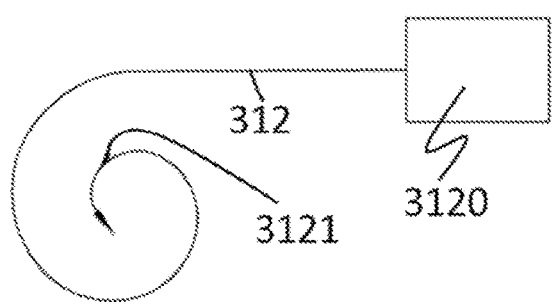
Figure 10D:
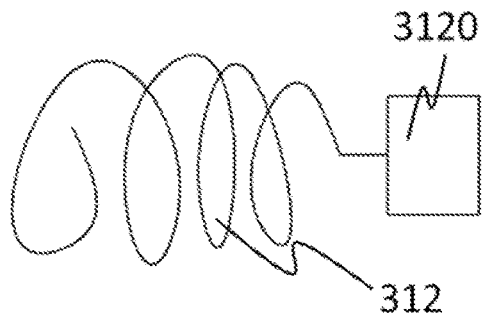
Figure 10E:
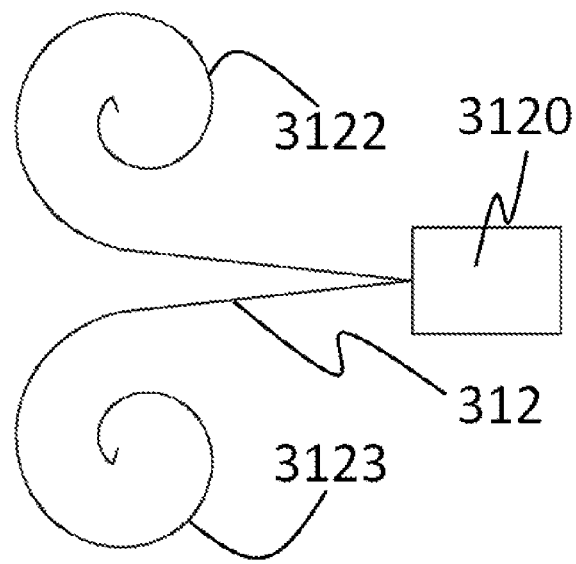
Figure 10F:
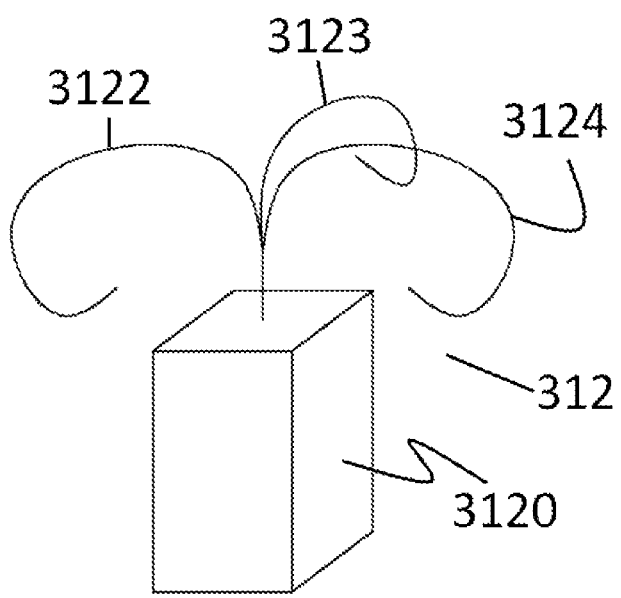

In one embodiment, Referring to FIG. 10A, the most distal end of the anchor 312 is a sharp. Referring to FIG. 10B to FIG. 10D, the distal section of the anchor 312 is pre-shaped to one or a combination of several of the following shapes: a spiral, a circle, an arc, a combination of an arc line and a straight line, a bifurcated double hook, a 3D curved form, a multi-segment curved form. The proximal end of the anchor 312 is provided with an anti-disengagement end 3120, and the distal section of the anchor 312 is further provided with a barb 3121 for reinforcing the anchoring effect after piercing into the autologous tissue of the patient. Referring to FIG. 10E, the distal section of the anchor 312 has two bifurcations 3122, 3123 to enhance the anchoring effect. Referring to FIG. 10F, the distal section of the anchor 312 has three bifurcations 3122, 3123, 3124 to enhance the anchoring effect.

Finally, it should be noted that the above mentioned only illustrate preferred embodiments of the present invention, but not to limit the scope of the invention, and any amendments, equivalent replacements, improvements and so on made within the spirits and principles of the present invention all should be included in the protection scope of the present invention.

The invention claimed is:

1. A prosthesis for preventing valve regurgitation, comprising a fixation unit, a connection piece and a closure assisting piece, the fixation unit comprising a fixation piece and an anchor, a distal section of the connection piece being connected to a proximal section of the fixation piece, a proximal section of the connection piece being connected to a distal section of the closure assisting piece, the connection piece being flexible such that the connection piece and the closure assisting piece connected thereto are movable with a movement of a valve leaflet, the fixation piece being secured to an atrial wall or a valve annulus of a patient by the anchor, a deployed width of the fixation piece being less than two thirds of a circumference of the valve tissue annulus, the closure assisting piece is configured to be between autologous valve leaflets of the patient when the prosthesis is in a free state, a maximum width of the closure assisting piece being less than a maximum width of a single autologous valve leaflet, a proximal end of the anchor being provided with an anti-disengagement end, a distal end of the anchor is configured for being fixed in the atrial wall or the valve annulus of the patient, the proximal end of the anchor is configured for being located outside the atrial wall or the valve annulus of the patient; there is a channel for blood flowing therethrough between the closure assisting piece and the fixation piece; the connection piece is entirely covered with a film, a hole is provided in the film, and the hole is the channel for blood flowing therethrough.

2. The prosthesis for preventing valve regurgitation according to claim 1, wherein the closure assisting piece is a single piece, multiple pieces, or a combination of the single piece and the multiple pieces.

3. The prosthesis for preventing valve regurgitation according to claim 2, wherein the closure assisting piece is a grid structure, or the closure assisting piece is a polymer piece or an animal-derived material piece, the closure assisting piece is provided with a hole when the closure assisting piece is the polymer piece or the animal-derived material piece.

4. The prosthesis for preventing valve regurgitation according to claim 1, wherein the anchor is connected to the fixation piece.

5. The prosthesis for preventing valve regurgitation according to claim 1, wherein the fixation piece and the connection piece are integrated as one piece.

6. The prosthesis for preventing valve regurgitation according to claim 1, wherein the connection piece is in a form of sheet, strip, or filament, or the connection piece is a combination of the above-mentioned structures.

7. The prosthesis for preventing valve regurgitation according to claim 1, wherein the fixation piece is a flexible polymer sheet or a polymer mesh.

8. The prosthesis for preventing valve regurgitation according to claim 1, wherein the fixation piece has a frame structure consisting of a plurality of support rods; or the frame structure is a waved structure or a zigzag shaped structure made of metallic shape memory material wire; or the frame structure is formed in a lattice pattern; or the frame structure is a combination of the above-described structures.

9. The prosthesis for preventing valve regurgitation according to claim 8, wherein in the free state of the prosthesis, the distal section of the frame structure is an arc shaped structure along a circumference of the valve annulus.

10. The prosthesis for preventing valve regurgitation according to claim 8, wherein the frame structure is covered with a film, the film is connected to the frame structure through sintering, welding, gluing, or stitching, a material of the film comprises PTFE, polyethylene, polypropylene, polyester, or an animal-derived material.

11. The prosthesis for preventing valve regurgitation according to claim 1, wherein the closure assisting piece is provided with an adjusting member, the adjusting member is a metal wire or a polymer wire, one end of the metal wire or the polymer wire is connected to the closure assisting piece, and the other end of the metal wire or the polymer wire is connected to a ventricle or an apex of a heart.

12. The prosthesis for preventing valve regurgitation according to claim 1, wherein the proximal end of the closure assisting piece is provided with a deploying device, and the deploying device is made of a metal wire or a polymer wire.

13. The prosthesis for preventing valve regurgitation according to claim 1, wherein a most distal end of the anchor is a sharp, and a distal section of the anchor is in a preset shape, the distal section of the anchor is pre-shaped into one or a combination of following shapes: a spiral, a circle, an arc, a combination of an arc line and a straight line, a bifurcated double hook, a 3D curved form, a multi-segment curved form, the distal end of the anchor has no barbs, has a barb, or has a plurality of barbs.

14. A prosthesis for preventing valve regurgitation, comprising a fixation unit, a connection piece and a closure assisting piece, the fixation unit comprising a fixation piece and an anchor, a distal section of the connection piece being connected to a proximal section of the fixation piece, a proximal section of the connection piece being connected to a distal section of the closure assisting piece, the connection piece being flexible such that the connection piece and the closure assisting piece connected thereto are movable with a movement of a valve leaflet, the fixation piece being secured to an atrial wall or a valve annulus of a patient by the anchor, a deployed width of the fixation piece being less than two thirds of a circumference of the valve tissue annulus, the closure assisting piece is configured to be between autologous valve leaflets of the patient when the prosthesis is in a free state, a maximum width of the closure assisting piece being less than a maximum deployed width of a single autologous valve leaflet, a proximal end of the anchor being provided with an anti-disengagement end, a distal end of the anchor is configured for being fixed in the atrial wall or the valve annulus of the patient, the proximal end of the anchor is configured for being located outside the atrial wall or the valve annulus of the patient; the connection piece is in a form of sheet, strip, or filament, or the connection piece is a combination of the above-mentioned structures; the connection piece is entirely covered with a film, a hole is provided in the film, and the hole is the channel for blood flowing therethrough.

* * * * *